United States Patent
Provencal et al.

(10) Patent No.: US 8,436,200 B2
(45) Date of Patent: May 7, 2013

(54) PROCESS FOR MAKING (R)-3-(2,3-DIHYDROXYPROPYL)-6-FLUORO-5-(2-FLOURO-4-IODOPHENYLAMINO)-8-METHYLPYRIDO[2,3-D]PYRIMIDINE-4,7(3H,8H)-DIONE AND INTERMEDIATES THEREOF

(75) Inventors: David Paul Provencal, San Diego, CA (US); Yuxin Zhao, San Diego, CA (US); Todd Miller, San Diego, CA (US); Jonathon S. Salsbury, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/421,421

(22) Filed: Mar. 15, 2012

(65) Prior Publication Data

US 2012/0264967 A1 Oct. 18, 2012

Related U.S. Application Data

(62) Division of application No. 12/617,536, filed on Nov. 12, 2009, now abandoned.

(60) Provisional application No. 61/115,646, filed on Nov. 18, 2008.

(51) Int. Cl.
*C07C 69/74* (2006.01)

(52) U.S. Cl.
USPC .............................................................. 560/1

(58) Field of Classification Search ............... 560/1
See application file for complete search history.

(56) References Cited

U.S. PATENT DOCUMENTS

| 8,030,317 B2 | 10/2011 | Dong |
| 2008/0255160 A1 | 10/2008 | Dong |

FOREIGN PATENT DOCUMENTS

| WO | WO/2008/016184 | 2/2008 |
| WO | WO/2008/079814 | 7/2008 |

OTHER PUBLICATIONS

Threlfall, Terence L. "Analysis of Organic Polymorphs. A Review" The Analyst, Oct. 1, 1995, vol. 120, p. 2463, col. 1-col. 2, XP009026967.

*Primary Examiner* — Paul V. Ward
(74) *Attorney, Agent, or Firm* — David M. Stemerick; Mitchell R. Brustein

(57) ABSTRACT

The present invention relates generally to processes of making (R)-3-(2,3-Dihydroxypropyl)-6-fluoro-5-(2-fluoro-4-iodophenylamino)-8-methylpyrido[2,3-d]pyrimidine-4,7(3H,8H)-dione, intermediates thereof, and a process for making a particular polymorph of (R)-3-(2,3-Dihydroxypropyl)-6-fluoro-5-(2-fluoro-4-iodophenylamino)-8-methylpyrido[2,3-d]pyrimidine-4,7(3H,8H)-dione.

2 Claims, No Drawings

PROCESS FOR MAKING (R)-3-(2,3-DIHYDROXYPROPYL)-6-FLUORO-5-(2-FLOURO-4-IODOPHENYLAMINO)-8-METHYLPYRIDO[2,3-D]PYRIMIDINE-4,7(3H,8H)-DIONE AND INTERMEDIATES THEREOF

RELATED APPLICATION

This is a divisional application of U.S. application Ser. No. 12/617,536, filed Nov. 12, 2009, which claims the benefit of U.S. Provisional Application No. 61/115,646, filed Nov. 18, 2008, which are incorporated herein by reference in their entirety.

FIELD OF THE INVENTION

The present invention relates generally to chemical synthesis and preparation of a certain polymorphic form.

BACKGROUND OF THE INVENTION

The present invention relates to an inhibitor of MEK and/or ERK activity useful for the treatment a variety of cancerous and non-cancerous disorders, including brain, lung, squamous cell, bladder, gastric, pancreatic, breast, head, neck, renal, kidney, ovarian, prostate, colorectal, colon, epidermoid, esophageal, testicular, gynecological or thyroid cancer; restenosis; benign prostatic hypertrophy (BPH)); pancreatitis; kidney disease; pain; vasculogenesis or angiogenesis (e.g., tumor angiogenesis); acute and chronic inflammatory disease such as rheumatoid arthritis, atherosclerosis, inflammatory bowel disease; skin diseases such as psoriasis, eczema, and scleroderma; diabetes; diabetic retinopathy; retinopathy of prematurity; age-related macular degeneration; asthma; neutrophil chemotaxis; septic shock; multiple sclerosis; chronic obstructive pulmonary disease; and others. Specifically the present invention relates to (R)-3-(2,3-dihydroxypropyl)-6-fluoro-5-(2-fluoro-4-iodophenylamino)-8-methylpyrido[2,3-d]pyrimidine-4,7(3H,8H)-dione, see PCT Publication No. WO2008/079814 published Jul. 3, 2008.

SUMMARY OF THE INVENTION

The present invention provides a novel process for making (R)-3-(2,3-dihydroxypropyl)-6-fluoro-5-(2-fluoro-4-iodophenylamino)-8-methylpyrido[2,3-d]pyrimidine-4,7(3H,8H)-dione, characterized by and comprising the steps of reacting a compound of the formula

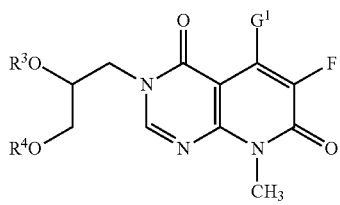

wherein $G^1$ is halogen and $R^3$ and $R^4$ are independently selected from the group consisting of hydrogen and suitable hydroxyl protecting groups with 2-fluoro-4-iodoaniline to give a compound of the formula

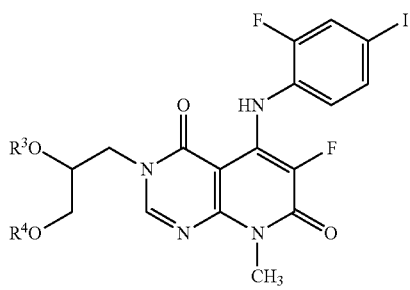

wherein $R^3$ and $R^4$ are as defined above and optional deprotection and optional resolution.

The present invention also provides intermediates below: a compound of the formula (a)

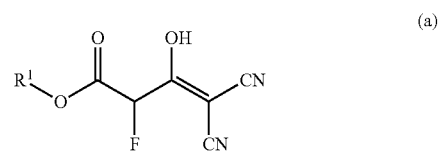

wherein $R^1$ is a suitable carboxy protecting group; 4,4-dicyano-1-fluoro-3-hydroxy-N-methylbut-3-enamide; a compound of the formula (b)

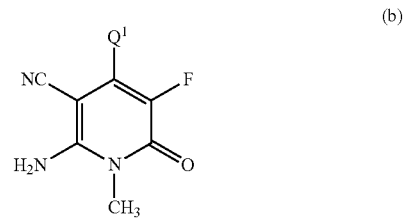

wherein $Q^1$ is selected from the group consisting of amino, hydroxyl and halogen; a compound the of formula (c)

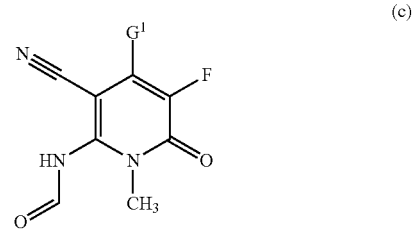

wherein $G^1$ is halogen; a compound of the formula (d)

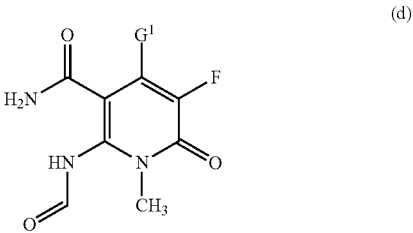

wherein $G^1$ is halogen; a compound of formula (e)

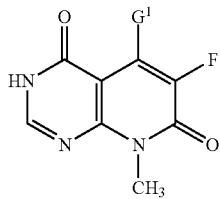

(e)

wherein $G^1$ is halogen; and a compound of the formula (f)

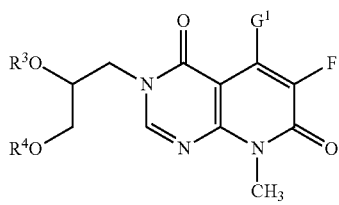

(f)

wherein $G^1$ is halogen and $R^3$ and $R^4$ are independently selected from the group consisting of hydrogen and suitable hydroxy protecting groups. The present invention also provides a process for making Form A polymorph of (R)-3-(2,3-dihydroxypropyl)-6-fluoro-5-(2-fluoro-4-iodophenylamino)-8-methylpyrido[2,3-d]pyrimidine-4,7(3H,8H)-dione, comprising crystallizing (R)-3-(2,3-dihydroxypropyl)-6-fluoro-5-(2-fluoro-4-iodophenylamino)-8-methylpyrido[2,3-d]pyrimidine-4,7(3H,8H)-dione from a solvent at a temperature of about greater than about 40° C.

DETAILED DESCRIPTION OF THE INVENTION

The term "suitable carboxy protecting groups" refers groups commonly employed to protect the carboxy hydrogen during certain synthetic steps but can be later removed as desired. The selection and use of suitable carboxy protecting groups is well known and appreciated in the art. Examples of suitable carboxy protecting groups include $C_{1-6}$ alkyl, such as methyl, and t-butyl; $C_{3-8}$ cycloalkyl; $C_{1-20}$ substituted alkyl carboxy protecting groups; silyl containing carboxy protecting groups; and the like.

The term "$C_{1-6}$ alkyl" refers to a saturated, straight or branched chain having one to six carbon atoms.

The term "$C_{3-8}$ cycloalkyl" refers to a saturated, optionally branched ring having three to eight carbon atoms. Examples include cyclopentyl and cyclohexyl.

The term "$C_{1-20}$ substituted alkyl carboxy protecting groups" refers to a $C_{1-6}$ alkyl, most typically methyl and ethyl, having a various substituents used in carboxy protecting groups. Examples of $C_{1-20}$ substituted alkyl carboxy protecting groups include methoxymethyl, methylthiomethyl, benzyloxymethyl, 2-methoxyethoxymethyl, 2,2,2-trichloroethoxymethoxy, 2-(trimethylsilyl)ethoxymethyl, tetrahydropyranyl, tetrahydrofuranyl, 2,2,2-chloroethyl, 2-haloethyl, 2-methylthioethyl, picolyl, allyl, and the like. Also included are optionally substituted benzyl, such as benzyl, p-methyoxybenzyl, 3,4-dimethoxybenzyl, o-nitrobenzyl, p-nitrobenzyl, p-bromobenzyl, p-chlorobenzyl, p-cyanobenzyl, p-phenylbenzyl, and the like.

The term "silyl containing carboxy protecting groups, include trimethylsilyl, triethylsilyl, triisopropylsilyl, dimethylisopropylsilyl, dimethylhexylsilyl, t-butyldimethylsilyl, t-butyldiphenylsilyl, and the like.

The term "halo" or "halogen" refers to fluoro, chloro, bromo, and iodo.

The term "suitable hydroxy protecting groups" refers to groups commonly employed to protect the hydroxyl hydrogen during certain synthetic steps but can be later removed as desired. The selection and use of suitable hydroxy protecting groups is well known and appreciated in the art. Examples of suitable hydroxy protecting groups include $C_{1-6}$ alkyl, such as methyl, and t-butyl; $C_{1-20}$ substituted alkyl hydroxyl protecting groups; silyl containing hydroxyl protecting groups; 1,2-diol protecting groups; and the like.

The term "$C_{1-20}$ substituted alkyl hydroxyl protecting groups" refers to a $C_{1-6}$ alkyl, typically methyl and ethyl, having a various substituents used in hydroxy protecting groups. Examples of $C_{1-20}$ substituted alkyl hydroxy protecting groups include methoxymethyl, benzyloxymethyl, 2-methoxyethoxymethyl, and 2,2,2-trichloroethoxymethoxy, 2-(trimethylsilyl)ethoxymethyl, tetrahydropyranyl, 1-methoxycyclohexyl, tetrahydrofuranyl, 1,4-dioxan-2-yl, 2-ethoxyethyl, 2,2,2-chloroethoxyethyl; picolyl; allyl; trityl, and the like. Also included are optionally substituted benzyl, such as including benzyl, p-methyoxybenzyl, 3,4-dimethoxybenzyl, o-nitrobenzyl, p-nitrobenzyl, p-bromobenzyl, p-chlorobenzyl, p-cyanobenzyl, p-phenylbenzyl, and the like.

The term "silyl containing hydroxyl protecting groups" includes those silyl groups used as hydroxyl protecting groups, such as trimethylsilyl, triethylsilyl, triisopropylsilyl, dimethylisopropylsilyl, dimethylhexylsilyl, t-butyldimethylsilyl, t-butyldiphenylsilyl, tribenzylsilyl, triphenylsilyl, diphenylmethylsilyl, t-butylmethyoxyphenylsilyl, and the like.

The term "1,2-diol protecting groups" refers to hydroxyl protecting groups used to protect 1,2-diols with a shared group and include $C_{1-14}$ acetals and ketals, such as methylene, ethylidene, 1-t-butylethylidene, acetonide, cyclohexylidene, benzylidine, p-methoxybenzylidene, methoxymethylene, and the like; and silyl 1,2-diol protecting groups such as di-t-butylsilylene, 1,3-(1,1,3,3-tetraisopropyl)disiloxanylidine, and the like.

The term "suitable leaving group" refers to group with the meaning conventionally associated with it in synthetic organic chemistry, that is, a group capable of being displaced under alkylating conditions, for example chloro, bromo, iodo, sulfonyloxy groups, such as trifluoromethanesulfonyloxy, mesyloxy, benzenesulfonyloxy, tosyloxy, and nosyloxy, and the like.

The skilled person will appreciate that the compounds of the present invention may exist as tautomers. The present invention contemplates all tautomeric forms.

In another embodiment the invention provides a process for making (R)-3-(2,3-dihydroxypropyl)-6-fluoro-5-(2-fluoro-4-iodophenylamino)-8-methylpyrido[2,3-d]pyrimidine-4,7(3H,8H)-dione, characterized by and comprising the steps of reacting a compound of the formula

5

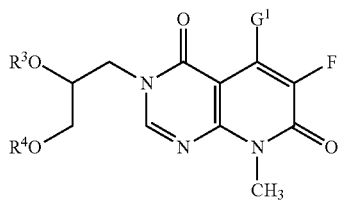

wherein $G^1$ is halogen and $R^3$ and $R^4$ are independently selected from the group consisting of suitable hydroxyl protecting groups with 2-fluoro-4-iodoaniline to give a compound of the formula

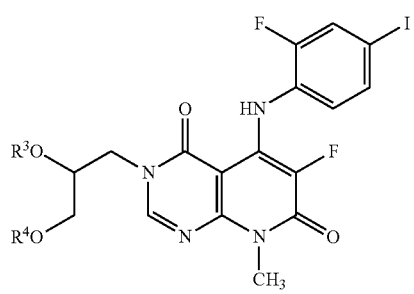

6 wherein $R^3$ and $R^4$ are independently selected form the group consisting of suitable hydroxyl protecting groups and deprotection and optional resolution.

In another embodiment the invention provides compounds of formula (f)

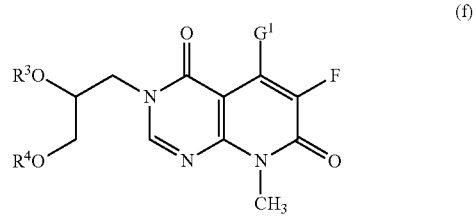

(f)

wherein $G^1$ is halogen and $R^3$ and $R^4$ are independently selected from the group consisting of suitable hydroxy protecting groups.

General synthetic procedures are set forth in Scheme A. All substituents, unless otherwise indicated, are as previously defined. The products in Scheme A can be recovered by conventional methods including extraction, evaporation, precipitation, chromatography, crystallization, trituration, and the like.

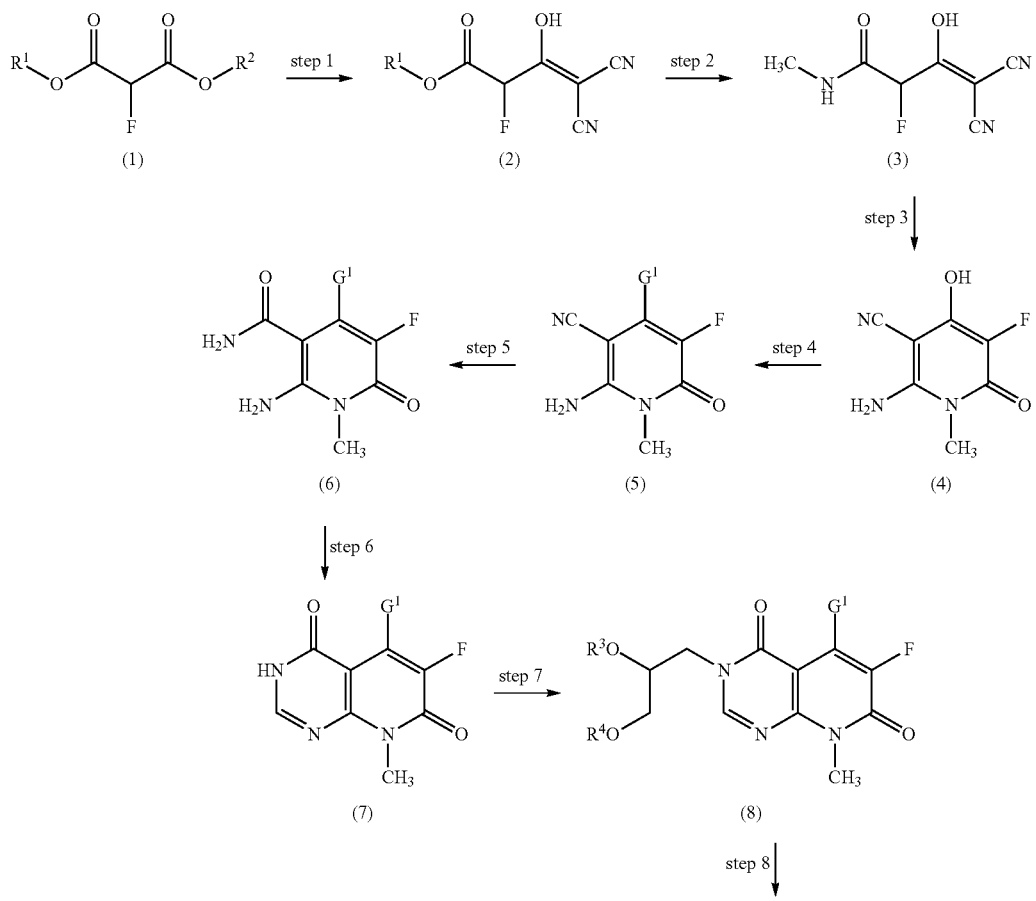

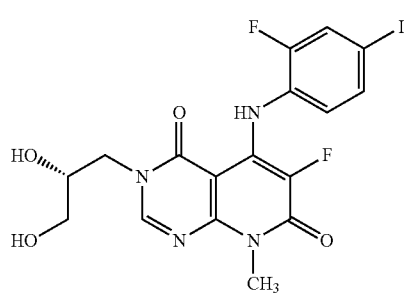

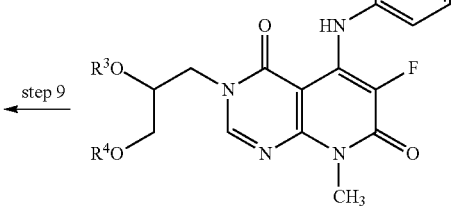

Scheme A, step 1 depicts the reaction of a compound of formula (1) with malononitrile to give a compound of formula (2). A compound of formula (1) is one wherein $R^1$ is a suitable carboxy protecting group and $R^2$ is a group which along with the oxygen to which it is attached is capable of being displaced, such as methoxy. For example, the reaction is carried out in a suitable solvent, such as tetrahydrofuran (THF), dioxane, dimethylsulfoxide (DMSO), dimethylformamide, dimethylacetamide, methanol, ethanol, isopropanol, acetonitrile, and the like. The reaction is carried out with the use of a suitable base, such as 1,8-diazabicyclo[5.4.0]undecane (DBU), 1,5-diazabicyclo[3.4.0]non-5-ene (DBN), diisopropylethylamine, triethyl amine, 1,4-diazabicyclo[2.2.2]octane (DABCO), metal alkoxides such as sodium methoxide and sodium ethoxide, sodium hydride, potassium t-butoxide, and the like. A molar excess of a suitable base can be used. Such reactions generally are carried out at temperature of from about −20° C. to 10° C. and typically require 1 to 72 hours.

Scheme A, step 2, depicts the reaction of a compound of formula (2) with N-methylamine to give the compound of formula (3). For example, the reaction is carried out in a solvent, such THF, dioxane, DMSO, dimethylformamide, dimethylacetamide, methanol, ethanol, isopropanol, water, and the like. An aqueous solution of N-methylamine can be used and the reagent is generally used in excess. The reaction is typically carried out at temperatures of from −20° C. to 50° C. and typically requires 1 to 16 hours.

Scheme A, step 3, depicts the cyclizaion of the compound of formula (3) to give the compound of formula (4). It is understood the compound of formula (3) first forms the compound 2,4-diamino-5-fluoro-1-methyl-6-oxo-1,6-dihydropyrimidine-carbonitrile, which is hydrolyzed to give a compound of formula (4). For example, the reaction is carried out in the presence of a base, such as sodium hydroxide, metal alkoxides, DBU, DABCO, and the like; in water, methanol, ethanol, isopropanol; at temperatures of from 10° C. to 50° C.; and typically require 2 to 12 hours.

Scheme A, step 4, depicts the reaction of a compound of formula (4) with a suitable halogen converting reagent to give a compound of formula (5) wherein $G^1$ is halogen. Suitable halogen converting reagent refers to a reagent capable of converting a hydroxyl to halogen, such as, phosphorous oxychloride, phosphorous pentachloride, phosphorous pentabromide, phosphorous oxybromide, thionyl chloride, thionyl bromide, bromine/triphenylphosphine, and the like.

For example, the reaction typically uses an excess of the selected suitable halogen converting agent is carried out in a solvent, such as THF, acetonitrile, and the like. In some cases the halogen converting reagent can be used as a solvent. The reaction is typically carried out at temperatures of from 0° C. to reflux temperature of the selected solvent and typically require 1 to 15 hours. The skilled person will recognize that adducts of certain halogen converting reagents may be formed and that such adducts are preferably hydrolyzed to optimize yields.

Scheme A, step 5, depicts the hydrolysis of a compound of formula (5) to give a compound of formula (6). For example, the reaction is carried out in water or dimethylformamide, dimethylacetamide, toluene, and the like containing water and in the presence of a suitable acid. The reaction is generally carried out at temperatures of from 50° C. to 100° C. and typically require 4 to 10 hours.

Scheme A, step 6, depicts the reaction of a compound of formula (6) with a formyl forming reagent and cyclization to give a compound of formula (7) wherein $G^1$ is as defined above. It is understood that the cyclization in step 6 involves a formyl intermediate and that the cyclization is carried out without isolation of the product from the formyl formation. For example, the formyl forming reaction is carried out in a solvent. The solvent selected will depend on the formyl forming reagent used, where that reagent is formic acid the solvent is usually water or the reaction is carried out in formic acid without water being added. The cyclization is carried out in a solvent such as water and is generally carried out in the presence of an acid, such as hydrochloric acid, sulfuric acid, phosphoric acid, and the like. The reactions are carried out at temperatures of from 50° C. to 100° C. and typically require 4 to 15 hours.

Scheme A, step 7, depicts the reaction of a compound of formula (7) with a 2,3-dihydroxypropyl transfer reagent to give a compound of formula (8). Step 7 can be carried out using a racemic or an enantiomerically pure 2,3-dihydroxypropyl transfer reagent. It is understood that the use of an enantiomerically pure 2,3-dihydroxypropyl transfer reagent generally provides an enantiomerically pure compound of formula (8). The use of an enantiomerically pure 2,3-dihydroxypropyl transfer reagent is preferred. 2,3-Dihydroxypropyl transfer reagents include compounds of the formulas (10) and (11) below:

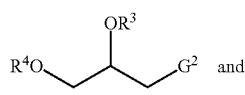

(10)

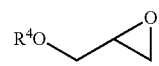

(11)

wherein $G^2$ is a suitable leaving group and $R^3$ and $R^4$ are hydrogen or suitable hydroxyl protecting groups and the stereochemistry is either racemic or enantiomerically pure.

Most conveniently, in compound (10) $R^3$ and $R^4$ are taken together to form a 1,2-diol protecting group. It is to be understood that step 7 may additionally include one or more deprotection and/or protection steps. For example, a compound of formula (10) may give rise to compound of formula (8) in which $R^3$ and $R^4$ are protecting groups, which may be deprotected, either partially or fully before step 8 to give either a compound of formula (9) in which $R^3$ or $R^4$ is hydrogen or to directly give a 3-(2,3-dihydroxypropyl)-6-fluoro-5-(2-fluoro-4-iodophenylamino)-8-methylpyrido[2,3-d]pyrimidine-4,7(3H,8H)-dione. Likewise, for example, a compound of formula (11) will give rise to compound of formula (8) in which $R^3$ is hydrogen and $R^4$ is hydrogen or a protecting group, which may be used in step 8 to give a compound of formula (9) in which $R^3$ is hydrogen and $R^4$ is a protecting group or deprotected before use to directly give a 3-(2,3-dihydroxypropyl)-6-fluoro-5-(2-fluoro-4-iodophenylamino)-8-methylpyrido[2,3-d]pyrimidine-4,7(3H,8H)-dione. In addition, for example, such a compound of formula (8) in which $R^3$ is hydrogen and $R^4$ is a protecting group may have a protecting group added at $R^3$ to give a fully protected compound of formula (8). Of course, other variations of protections and deprotections are possible and available to the skilled person, all of which are contemplated to be within the scope of the present process. As used herein the term "enantiomerically pure" refers to greater than 90%, preferably greater than 95%, more preferably greater than 97%, most preferably greater than 99% of the desired isomer. For example, the reaction is carried out in a solvent, such as THF, dimethylformamide, dimethylacetamide, N-methylpyrrolidone, dioxane, and the like. The reaction is carried out with the use of a suitable base, such as lithium hexamethyldisilazide, lithium diisopropylamide, potassium carbonate, cesium carbonate, metal alkoxides, such as potassium t-butoxide, amines, such as triethylamine, DBU, DBN, DABCO, and the like. The addition of base is usually carried out at temperature of from about −20° C. to 30° C. After addition of the protected 2,3-dihydroxyproply transfer reagent the temperature may be raised to about 20° C. to 80° C. The reaction typically requires 1 to 72 hours. Such reactions generally are carried out at temperature of from about −20° C. to 30° C. and typically require 1 to 72 hours.

Scheme A, step 8, depicts the reaction of a compound of formula (8) with 2-fluoro-4-iodoaniline to give a compound of formula (9). For example, the reaction is carried out in a solvent, such as THF, dimethylformamide, dimethylacetamide, and the like. The reaction is carried out with the use of a suitable base. Bases such as lithium hexamethyldisilazide, lithium diisopropylamide, and the like are preferred. The addition of base is typically carried out at temperature of from about −25° C. to 15° C. After the base is added the temperature may be raised to about 20° C. to 90° C. The reaction typically requires 1 to 72 hours.

Alternately, for example, the reaction can be carried out in the presence of catalyst, such as a palladium [0] or [II] catalyst. The palladium catalyst can be prepared with a phosphine ligand, such as $PPh_3$, $P(t-Bu)_3$, dppf, tricyclohexylphosphine, Xantphos, Dave's phos, bis(di-t-Butylphosphino)ferrocene, DEPphos, X-phos. The reaction is carried out in a solvent, such as THF and dioxane. The reaction is carried out with the use of a suitable base, such as sodium t-butoxide, potassium t-butoxide, potassium hydroxide, and sodium hydroxide. The reaction is typically carried out at temperature of from about 25° C. to 100° C. The reaction typically requires 16 to 72 hours.

Scheme A, step 9, depicts the deprotection of a compound of formula (9) to give (R)-3-(2,3-dihydroxypropyl)-6-fluoro-5-(2-fluoro-4-iodophenylamino)-8-methylpyrido[2,3-d]pyrimidine-4,7(3H,8H)-dione. The term "deprotection" refers to the procedure by which a protecting group is removed. Such deprotections of are well known an appreciated in the art. The use and removal of protecting groups is well known in the art. See for example, Protecting Groups in Organic Synthesis, Theodora Greene (Wiley-Interscience)).

In an additional, optional step, not shown, a racemic mixture is resolved to give enantiomerically pure product. It is also understood that the product of the present process may be used as a pharmaceutically acceptable salt which would be formed in an optional step, not shown, if desired.

It is understood that the order of certain steps is not critical in the process of the present invention. For example, while the introduction of $G^1$ is depicted in step 4, this group can be introduced at any point before the reaction with 2-fluoro-4-iodoaniline depicted in step 8. Additionally it is understood that an optional resolution, if necessary, can be carried out before or after step 9.

The synthetic process of the present invention allows for the preparation of (R)-3-(2,3-dihydroxypropyl)-6-fluoro-5-(2-fluoro-4-iodophenylamino)-8-methylpyrido[2,3-d]pyrimidine-4,7(3H,8H)-dione while avoiding the use of a fluorinating reagent in the last step. That is, the present invention provides a valuable process for making (R)-3-(2,3-dihydroxypropyl)-6-fluoro-5-(2-fluoro-4-iodophenylamino)-8-methylpyrido[2,3-d]pyrimidine-4,7(3H,8H)-dione characterized by the reaction of a compound of formula (8) with 2-fluoro-4-iodoaniline to give a compound of formula (9). Such a process avoids the use of costly and possible hazardous fluorinating regents in later steps which has significant advantages in large-scale manufacture.

The present invention also provides a process for making Form A polymorph of (R)-3-(2,3-dihydroxypropyl)-6-fluoro-5-(2-fluoro-4-iodophenylamino)-8-methylpyrido[2,3-d]pyrimidine-4,7(3H,8H)-dione by crystallizing (R)-3-(2,3-dihydroxypropyl)-6-fluoro-5-(2-fluoro-4-iodophenylamino)-8-methylpyrido[2,3-d]pyrimidine-4,7(3H,8H)-dione at a temperature of about 40° C. or more. The formation of Form A is generally carried out in a solvent. In practice suitable solvents $C_{1-3}$ carboxylic acid, $C_{3-7}$ alkylacetate, $C_{1-6}$ alcohol, $C_{2-8}$ ether, and $C_{3-7}$ alkanone. Anti-solvents, that is, a solvent or solvents in which the compound is less soluble than in the selected solvent can also be used. As used herein the term "$C_{1-3}$ carboxylic acid" refers to alkanoic acid having from one to three carbon atoms, for example, formic, acetic, and propionic acid; "$C_{3-7}$ alkylacetate" refers to straight or branched alkyl esters of acetic acid having a total of three to seven carbons; the term "$C_{1-6}$ alcohol" a straight or branched alkanols having from one to six carbon atoms, for example methanol, ethanol, n-propanol, iso-propanol, 1,3-propanediol, and the like; the term "$C_{2-8}$ ether" refers to a straight, branched, or cyclic alkyl ethers having a total of from two to eight carbon atoms, for example diethyl ether, methyl-t-butyl ether, THF, dioxane, and the like; and the term "$C_{3-7}$ alkanones" refers to a straight or branched alkyl chain having an oxo group and having a total of from three to seven carbon atoms, for example acetone and methyl ethyl ketone.

It is understood that the terms "crystallize," "crystallizing," and "crystallization" to complete dissolution followed by precipitation and slurry processes that do not involve complete dissolution. Slurry processes include those that encompass continuation of stirring following precipitation.

For example, non-Form A (R)-3-(2,3-dihydroxypropyl)-6-fluoro-5-(2-fluoro-4-iodophenylamino)-8-methylpyrido[2,3-d]pyrimidine-4,7(3H,8H)-dione is crystallized from a solvent at temperature of about 40° C. or higher. The temperature can range up to the reflux temperature of the selected solvent and is usually less than 115° C. Where the crystallization involves complete dissolution, a slow cooling is preferred. Crystallization to give Form A does not require complete dissolution. Slurry processes can be used. A slurry can be formed by processing without complete dissolution or by complete dissolution followed by processing after initial precipitation. In a slurry process the volume should be sufficient to provide free-flowing slurry.

In one embodiment non-Form A (R)-3-(2,3-dihydroxypropyl)-6-fluoro-5-(2-fluoro-4-iodophenylamino)-8-methylpyrido[2,3-d]pyrimidine-4,7(3H,8H)-dione is crystallized from a solvent at temperature of about 50° C. or higher. In another embodiment non-Form A (R)-3-(2,3-dihydroxypropyl)-6-fluoro-5-(2-fluoro-4-iodophenylamino)-8-methylpyrido[2,3-d]pyrimidine-4,7(3H,8H)-dione is crystallized from a solvent at temperature of about 60° C. or higher.

The solvent should be one in which (R)-3-(2,3-dihydroxypropyl)-6-fluoro-5-(2-fluoro-4-iodophenylamino)-8-methylpyrido[2,3-d]pyrimidine-4,7(3H,8H)-dione is somewhat soluble. The volume of solvent is not critical but should be kept to a minimal amount as a matter of convenience. Optionally, the crystallization may be seeded with Form A. Such processes generally require 2 hours to seven days. According to the present process Form A (R)-3-(2,3-dihydroxypropyl)-6-fluoro-5-(2-fluoro-4-iodophenylamino)-8-methylpyrido[2,3-d]pyrimidine-4,7(3H,8H)-dione may be prepared in substantially pure. The term "substantially pure" refers to greater than 90%, preferably greater than 97%, more preferably greater than 99%, and even more preferably greater than 99.8% polymorphic purity.

The starting material for the present crystallization process can be any form of (R)-3-(2,3-dihydroxypropyl)-6-fluoro-5-(2-fluoro-4-iodophenylamino)-8-methylpyrido[2,3-d]pyrimidine-4,7(3H,8H)-dione, including Form A, a non-Form A polymorph in admixture with Form A, or a non-Form A polymorph.

Form A can be characterized by X-ray diffraction. The peaks were measured using a powder diffractometer equipped with a copper source, primary beam monochromator, and position sensitive detector. The incident beam was collimated using a 1° divergence slit. The source was operated at 40 kV and 30 mA. X-ray powder diffraction data were collected from 3 degrees to 45 degrees using a step width of 0.04 degree. The diffractometer was well calibrated with a silicon standard. Form A was found to have the following peaks in degrees 2-theta, rounded to 2 significant figures (relative intensity): 11.03 (34%), 15.88 (15%), 16.26 (100%), 19.32 (90%), 20.11 (15%), 22.16 (23%), 26.66 (17%), 27.84 (33%), and 30.18 (17%).

Form A (R)-3-(2,3-dihydroxypropyl)-6-fluoro-5-(2-fluoro-4-iodophenylamino)-8-methylpyrido[2,3-d]pyrimidine-4,7(3H,8H)-dione is characterized by peaks at 11.03, 16.26, 19.32, 20.11, 22.16, or 27.84 2-theta, Form A (R)-3-(2,3-dihydroxypropyl)-6-fluoro-5-(2-fluoro-4-iodophenylamino)-8-methylpyrido[2,3-d]pyrimidine-4,7(3H,8H)-dione is also characterized by peaks at 16.26 and 19.32 2-theta; 16.26 and 27.84 2-theta; 19.32 and 27.84 2-theta; 11.03 and 16.26 2-theta; 11.03 and 19.32 2-theta; 11.03, 16.26 and 19.32 2-theta; 16.26, 19.32, and 27.84 2-theta; 19.32, 22.16, and 27.84 2-theta; 11.03, 16.26, 19.32, and 27.84 2-theta; and 11.03, 16.26, 19.32, 20.11, 22.16, and 27.84 2-theta.

It is recognized that the relative intensity of X-ray diffraction peaks can be dependent on preferred orientation and other factors. Therefore, a sample of Form A may require processing to mitigate such factors, such as grinding the sample in an agate mortar and pestle or other measures. It is understood that differences in relative intensity of the diffraction peaks does not preclude an acquired pattern from being consistent with Form A.

Form A can also be characterized by differential scanning calorimetry. A thermogram of Form A provides a single endothermic event at 238-240° C. which was consistent with a melt.

In order that the invention be more fully understood the foregoing processes are exemplified below. These examples are understood to be illustrative only and are not intended to limit the scope of the invention in any way:

Example 1

2-Amino-5-fluoro-4-hydroxy-1-methyl-6-oxo-1,6-dihydropyridine-carbonitrile

Combine dimethylfluoromalonate (10 g, 0.066 mol) and malononitrile (4.4 g, 0.066 mol) in THF (50 mL) and cool to about −35° C. Add DBU (20 mL, 0.128 mol) over about 20 minutes while keeping the internal temperature below about −25° C. When the addition of DBU is complete, slowly warm to ambient temperature. After 18 hours, slowly add aqueous methylamine (40%, 30 mL, 0.44 mol). After 2 hours, add aqueous sodium hydroxide (10 M, 1 mL). After 3 hours, evaporate in vacuo to obtain a largely aqueous residue, cool to about 0° C., add concentrated hydrochloric acid (about 5 mL) to a pH of about 1 to give a solid. Collect the solid by filtration and rinse with water and ethanol (10 mL) to give the title compound. $^1$H NMR (400 MHz, DMSO-d6) δ11.71 (s, 1H), 7.29 (s, 2H), 3.27 (s, 3H); $^{13}$C NMR (100 MHz, DMSO-d6) δ154.7 (d, J=21.9 Hz), 153.1, 151.4 (d, J=13.2 Hz), 129.5 (d, J=211 Hz), 115.4 (d, J=3.7 Hz), 63.2 (d, J=2.9 Hz), 28.7; $^{19}$F NMR (376 MHz, DMSO-d6) δ−178.9; MS (M+H)+m/z calcd 184.0. found 184.0.

Example 2

2-Amino-5-fluoro-4-chloro-1-methyl-6-oxo-1,6-dihydropyridine-carbonitrile

Combine 2-amino-5-fluoro-4-hydroxy-1-methyl-6-oxo-1,6-dihydropyridine-carbonitrile (30.0 g, 0.164 mol) and anhydrous acetonitrile (150 mL). Slowly add phosphorous oxychloride (37 mL). After addition is complete heat to reflux. After 3 hours, cool to ambient temperature and then in an ice-bath. Add another portion of acetonitrile (150 mL). Slowly add to ice-water (300 mL, 10 volumes). Heat to about 50° C. After 5 hours, cool in an ice bath to give a solid, filter, rinse the solid with water, and dry in vacuo to give the title compound. $^1$H NMR (400 MHz, DMSO-d6) δ7.73 (s, 2H). 3.33 (s, 3H); $^{13}$C NMR (100 MHz, DMSO-d6) δ153.3 (d, J=32.9 Hz), 139.2, 136.9, 128.5 (d, J=16.9 Hz), 115.3 (d, J=2.2 Hz), 68.1, 29.7 (d, J=1.4 Hz); $^{19}$F NMR (376 MHz, DMSO-d6) δ−152.0; MS (M+H)+m/z calcd 202.0. found 202.0. Combine the title compound (4.4 g) in 40 mL of dimethylacetamide (40 mL) and heat to 38° C. Add activated carbon (4.4 g). After 30 minutes filter through Celite®, rinse with dimethylacetamide, and add water to the filtrate, then cool in an ice bath to give a solid. Collect the solid by filtration, rinse with water (20 mL), and dry in vacuo at give the title compound.

Example 3

5-Chloro-6-fluoro-8-methylpyrido[2,3-d]pyrimidine-4,7(3H, 8H)-dione

Combine 2-amino-5-fluoro-4-chloro-1-methyl-6-oxo-1,6-dihydropyridine-carbonitrile (33.0 g, 0.164 mol) and 99% formic acid (264 mL, 8 volumes) in a dried vessel. Heat to 70° C. When a solution is formed, add concentrated aqueous hydrochloric acid (165 mL, 5 volumes). After 20 hours, add another portion of concentrated aqueous hydrochloric acid (35 mL) and heated at 70° C. for another 4 h. Then cool the reaction mixture to the ambient temperature and add ice-water (350 mL, 10 volumes). Cool in an ice bath to give a solid. After 30 minutes, collect the solid by filtration, rinse with water (2×30 mL), and dry in vacuo to give the title compound. $^1$H NMR (400 MHz, DMSO-d6) δ12.96 (s, 1H), 8.35 (s, 1H). 3.61 (s, 3H); $^{13}$C NMR (100 MHz, DMSO-d6) δ157.7 (d, J=4.4 Hz), 154.6 (d, J=26.4 Hz), 151.2 (d, J=2.2 Hz), 149.9, 146.4 (d, J=242 Hz), 125.0 (d, J=16.9 Hz), 99.94, 29.8; $^{19}$F NMR (376 MHz, DMSO-d6) δ −133.8; MS (M+H)+ m/z calcd 230.0. found 230.0.

Example 4.1

5-Chloro-6-fluoro-8-methylpyrido[2,3-d]pyrimidine-4,7(3H,8H)-dione

Combine 2-amino-5-fluoro-4-chloro-1-methyl-6-oxo-1,6-dihydropyridine-carbonitrile (4.97 g, 246 mmol) and 99% formic acid (40 mL, 8 volumes) in a dried vessel. Heat to 80° C. When a solution is formed add aqueous 9 N sulfuric acid (25 mL, 5 volumes). After 20 hours, cool ambient temperature and add ice-water (50 mL, 10 volumes) with stirring. Cool in an ice bath to give a solid. After 30 minutes, collect the solid by filtration, rinse with water (2×5 mL), and dry in vacuo to give the title compound.

Example 4.2

5-Chloro-6-fluoro-8-methylpyrido[2,3-d]pyrimidine-4,7(3H,8H)-dione

Combine 2-amino-5-fluoro-4-chloro-1-methyl-6-oxo-1,6-dihydropyridine-carbonitrile (50.0 g, 0.248 mol) and 88% formic acid (400 mL, 8 volumes) in a dried vessel. Add concentrated (96%) sulfuric acid (125 mL, 2.5 volumes) slowly added to the mixture at below room temperature to give a solution. Heat at 70° C. for 24 hours. Cool below the ambient temperature and slowly add water (625 mL, 12.5 volumes) while maintaining the temperature below ambient temperature to give a slurry. After 4 hours, collect the solid by filtration, rinse with water (2×100 mL), and dry in vacuo to give the title compound.

Example 5.1

(R)-5-Chloro-3-((2,2-dimethyl-1,3-dioxolan-4-yl)methyl)-6-fluoro-8-methylpyrido[2,3-d]pyrimidine-4,7(3H,8H)-dione Combine 5-chloro-6-fluoro-8-methylpyrido[2,3-d]pyrimidine-4,7(3H,8H)-dione (20.0 g, 87.1 mmol) and dimethylacetamide (100 mL, 5 volumes) in a dried vessel. Cool in an ice-bath then add lithium hexamethyldisilazide (1 M/L in THF, 96.0 mL, 96.0 mmol). After 5 minutes, add (S)-2,2-dimethyl-1,3-dioxolan-4-yl)methyl 4-nitrobenzenesulfonate (30.4 g, 95.7 mmol). Slowly heat to 60° C. After 15 hours, cool to ambient temperature and evaporate the THF in vacuo, cool the remaining mixture in an ice-bath and then add ice-water (60 mL, 3 volumes) to give a solid. Collect the solid by filtration, rinse with water, and dry in vacuo. Combine the solid (24.0 g) in iso-propyl acetate (170 mL, ~7 volumes) and heat to reflux. After 3 hours, cool to ambient temperature to give a solid. Collect the solid by filtration, rinse with iso-propylacteate/heptane (20 mL, 1:1 by volume), and dry in vacuo to give the title compound. $^1$H NMR (400 MHz, DMSO-d6) δ8.58 (s, 1H), 4.38 (m, 1H), 4.22 (dd, 1H, J=13.6, 3.6 Hz), 4.07 (dd, 1H, J=8.4, 6.4 Hz), 3.94 (dd, 1H, J=13.6, 7.6 Hz), 3.76 (dd, 1H, J=8.8, 5.2 Hz), 3.61 (s, 3H), 1.37 (s, 3H), 1.24 (s, 3H); $^{13}$C NMR (100 MHz, DMSO-d6) δ157.0 (d, J=3.6 Hz), 154.5 (d, J=25.6 Hz), 152.4, 150.5 (d, J=2.2 Hz), 146.8 (d, J=243 Hz), 124.9 (d, J=17.6 Hz), 109.1, 99.1, 72.3, 66.1, 48.8, 29.7, 26.5, 25.0; HRMS (QSTAR) (M+H)+ m/z calcd 344.0808. found 344.0799.

Example 5.2

(R)-5-Chloro-3-((2,2-dimethyl-1,3-dioxolan-4-yl)methyl)-6-fluoro-8-methylpyrido[2,3-d]pyrimidine-4,7(3H,8H)-dione Combine 5-chloro-6-fluoro-8-methylpyrido[2,3-d]pyrimidine-4,7(3H,8H)-dione (5.00 g, 21.8 mmol), (S)-(2,2-dimethyl-1,3-dioxolan-4-yl)methyl-4-nitrobenzenesulfonate (7.60 g, 24.0 mmol), and N-methylpyrrolidinone (25.0 mL, 259 mmol). Add 1,8-Diazabicyclo[5.4.0]undec-7-ene (3.58 mL, 24.0 mmol) to the suspension. Heat to 60° C. and stir overnight. Add isopropyl acetate (50.0 mL, 427 mmol) followed by water (50.0 mL, 2780 mmol) while maintaining the temperature above 50° C. Stir at 60° C. for 1 hour, separate the phases and transfer the aqueous phase to a flask. Add isopropyl acetate (50.0 mL, 427 mmol) to the flask and stir at 60° C. for 1 hour and then separate the layers. Combine the organic phases and concentrate under vacuum to about 25 mL to give a solid. Cool to ambient temperature and stir for no longer than 2 hours, collect the solid by filtration, dry under vacuum overnight to give the title compound.

Example 6.1

(R)-3-((2,2-Dimethyl-1,3-dioxolan-4-yl)methyl)-6-fluoro-5-(2-fluoro-4-iodophenylamino)-8-methylpyrido[2,3-d]pyrimidine-4,7(3H,8H)-dione Combine (R)-5-chloro-3-((2,2-dimethyl-1,3-dioxolan-4-yl)methyl)-6-fluoro-8-methylpyrido[2,3-d]pyrimidine-4,7(3H,8H)-dione (5.00 g, 14.5 mmol) and 2-fluoro-4-iodoaniline (3.45 g, 14.5 mmol) in THF (25 mL). Cool in an ice-bath. Add lithium hexamethyldisilazide (1.0 M in THF, 36.4 mL, 36.4 mmol) maintaining the temperature below about 10° C. After 10 minutes, warm to ambient temperature. After 30 minutes, heat to 55° C. After 20 hour, cool to ambient temperature, add dimethylacteamide (35 mL) and evaporate in vacuo to remove most of the THF. Cool the remaining mixture in an ice-bath then add water (17.5 mL) to form a solid. Add water (20 mL), then collect the solid by filtration, rinse with water (3×15 mL), heptane (15 mL), and dry in vacuo to give the title compound. $^1$H NMR (400 MHz, DMSO-d6) δ10.14 (s, 1H), 8.60 (s, 1H), 7.68 (d, 1H, J=10.4, 2.0 Hz), 7.52 (d, 1H, J=8.8 Hz), 6.96 (td, 1H, J=8.8, 6.0 Hz), 4.41 (m, 1H), 4.25 (dd, 1H, J=13.6, 3.6 Hz), 4.06 (dd, 1H, J=8.8, 6.4 Hz), 3.98 (dd, 1H, J=13.6, 7.6 Hz), 3.78 (dd, 1H, J=9.2, 5.6 Hz), 3.58 (s, 3H), 1.37 (s, 3H), 1.23 (s, 3H); $^{13}$C NMR (100 MHz, DMSO-d6) δ161.1 (d, J=4.4 Hz), 155.7 (d, J=8.8 Hz), 155.4, 153.3, 151.1 (d, J=109 Hz), 135.6, 133.6 (d, J=7.3 Hz), 133.1 (d, J=3.7 Hz), 127.9 (d, J=13.2 Hz), 125.2 (d, J=6.5 Hz), 123.9 (d, J=21.9 Hz), 109.1, 95.1 (d, J=4.4 Hz), 87.1 (d, J=7.3 Hz), 72.2, 66.1, 48.9, 28.8, 26.6, 25.0; $^{19}$F NMR (376 MHz, DMSO-d6) δ -124.5, -149.3; MS (M+H)+ m/z calcd 545.0. found 545.0.

Example 6.2

(R)-3-((2,2-Dimethyl-1,3-dioxolan-4-yl)methyl)-6-fluoro-5-(2-fluoro-4-iodophenylamino)-8-methylpyrido[2,3-d]pyrimidine-4,7(3H,8H)-dione Combine (R)-5-chloro-3-((2,2-dimethyl-1,3-dioxolan-4-yl)methyl)-6-fluoro-8-methylpyrido[2,3-d]pyrimidine-4,7(3H,8H)-dione (4.00 g, 11.6 mmol), 2-fluoro-4-iodoaniline (2.76 g, 11.6 mmol) and tetrahydrofuran (16.0 mL, 197 mmol). Cool to 0° C. to 5° C. in an ice bath, add 1.0 M lithium hexamethyldisilazide in tetrahydrofuran (23.3 mL, 23.3 mmol) while keeping the temperature below 10° C. Agitate in an ice bath for no less than 30 min and then warm to ambient temperature and stir overnight. Add water (20.0 mL) and methylene chloride (40.0 mL) and agitate, then separate the phases. Combine the organic phase and 40 mL of water, adjust the pH to 7 with 2 N HCl. Separate the organic phase extract with water (20 mL), dry over $MgSO_4$, concentrate to 20 mL to give a solid. Add isopropyl acetate (40.0 mL, 342 mmol) to the suspension, stir at ambient temperature for no less than 2 hours, collect the solid by filtration, rinse with isopropyl acetate (20 mL), and dry overnight at 30° C. under vacuum to give the title compound.

Example 7

(R)-3-((2,2-Dimethyl-1,3-dioxolan-4-yl)methyl)-6-fluoro-5-(2-fluoro-4-iodophenylamino)-8-methylpyrido[2,3-d]pyrimidine-4,7(3H,8H)-dione Combine (R)-5-chloro-3-((2,2-dimethyl-1,3-dioxolan-4-yl)methyl)-6-fluoro-8-methylpyrido[2,3-d]pyrimidine-4,7(3H,8H)-dione (0.050 g, 0.15 mmol) and 2-fluoro-4-iodoaniline (0.052 g, 0.22 mmol) in de-gassed dioxane (2.0 mL). Add palladium acetate (1.6 mg) and Xantphos (8.5 mg) and sodium t-butoxide (35 mg). Heat to 85° C. After 2 hours, dilute with ethyl acetate, wash with aqueous hydrochloric acid and then brine, dry over sodium sulfate, and concentrate in vacuo to give a residue. Purify the residue with flash chromatography eluting with ethyl acetate/hexane to give the title compound.

Example 8.1

(R)-3-(2,3-Dihydroxypropyl)-6-fluoro-5-(2-fluoro-4-iodophenylamino)-8-methylpyrido[2,3-d]pyrimidine-4,7(3H,8H)-dione Combine (R)-3-((2,2-dimethyl-1,3-dioxolan-4-yl)methyl)-6-fluoro-5-(2-fluoro-4-iodophenylamino)-8-methylpyrido[2,3-d]pyrimidine-4,7(3H,8H)-dione (24.75 g, 45.58 mmol) and ethanol (250 mL). Add aqueous 9N sulfuric acid (50 mL) over 5 minutes. Heat to 75° C. After 2 hour, cool to ambient temperature and then cool in an ice bath to give a solid. Collect the solid by filtration, rinse with ethanol (3×30 mL), and dry to give the title compound. $^1$H NMR (400 MHz, DMSO-d6) δ 10.24 (s, 1H), 8.52 (s, 1H), 7.69 (dd, 1H, J=10.4, 1.8 Hz), 7.52 (d, 1H, J=8.6 Hz), 6.98 (m, 1H), 5.14 (brs, 1H), 4.83 (brs, 1H), 4.32 (dd, 1H, J=12.9, 2.5 Hz), 3.76 (m, 1H), 3.67 (dd, 1H, J=13.1, 12.9 Hz), 3.58 (s, 3H), 3.46 (ddd, 1H, J=10.9, 5.3, 5.1 Hz), 3.38 (m, 1H); $^{13}$C NMR (100 MHz, DMSO-d6) δ 161.3 (d, J=4.0 Hz), 155.6 (d, J=22.8 Hz), 154.6 (d, J=250 Hz), 152.0, 150.6, 134.3 (d, J=231 Hz), 133.8 (d, J=7.1 Hz), 133.1 (d, J=3.0 Hz), 127.8 (d, J=10.3 Hz), 125.3 (d, J=7.0 Hz), 123.9 (d, J=21.5 Hz), 95.0 (d, J=4.0 Hz), 87.1 (d, J=7.8 Hz), 68.0, 63.8, 50.1, 28.8; $^{19}$F NMR (376 MHz, DMSO-d6) δ -124.4, -149.8; MS (M+H)+m/z calcd 505.0. found 505.0.

Example 8.2

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Combine (R)-3-((2,2-dimethyl-1,3-dioxolan-4-yl)methyl)-6-fluoro-5-(2-fluoro-4-iodophenylamino)-8-methylpyrido[2,3-d]pyrimidine-4,7(3H,8H)-dione (0.50 g, 0.919 mmol), methanol (5.0 mL) and 6.00 M hydrochloric acid (0.50 mL, 3.0 mmol) and heat to 60° C. After 2 hours, cool to 50° C. and stir for 24 hours, then cool to ambient temperature, filter to collect the solid, rinse with methanol, and dry under vacuum at 30° C. to give the title compound.

Example 9

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (19.89 g) in methanol (300 mL), heat to 60° C., and stir. After 48 hours, cool to ambient temperature. After 30 minutes, collect the solid by filtration and dry at 40° C. in vacuo to give the title compound.

Example 10

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in ethyl acetate (2.0 mL). Seal, heat to 40° C., and stir. After 24 hours, cool to ambient temperature. Collect the solid by filtration and dry to give the title compound.

Example 11

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in ethanol (2.0 mL). Seal, heat to 40° C., and stir. After 24 hours, cool to ambient temperature. Collect the solid by filtration and dry to give the title compound.

Example 12

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in methanol (2.0 mL). Seal, heat to 40° C., and stir. After 24 hours, cool to ambient temperature. Collect the solid by filtration and dry to give the title compound.

Example 13

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in ethyl acetate (2.0 mL). Seal and stir at ambient temperature. After 24 hours, collect the solid by filtration and dry to give the title compound.

Example 14

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in ethanol (2.0 mL). Seal and stir at ambient temperature. After 48 hours, collect the solid by filtration and dry to give the title compound.

Example 15

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in methanol (2.0 mL). Seal and stir at ambient temperature. After 24 hours, collect the solid by filtration and dry to give the title compound.

Example 16

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in ethyl acetate (2.0 mL). Seal, heat to 40° C., and stir. After 30 minutes, add 5 mg of Form A. After 24 hours, cool to ambient temperature. Collect the solid by filtration and dry to give the title compound.

Example 17

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in ethanol (2.0 mL). Seal, heat to 40° C., and stir. After 30 minutes, add 5 mg of Form A. After 24 hours, cool to ambient temperature. Collect the solid by filtration and dry to give the title compound.

Example 18

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in methanol (2.0 mL). Seal, heat to 40° C., and stir. After 30 minutes, add 5 mg of Form A. After 24 hours, cool to ambient temperature. Collect the solid by filtration and dry to give the title compound.

Example 19

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in ethyl acetate (2.0 mL). Seal and stir at ambient temperature. After 30 minutes, add 5 mg of Form A. After 24 hours, collect the solid by filtration and dry to give the title compound.

Example 20

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in ethanol (2.0 mL). Seal and stir at ambient temperature. After 30 minutes, add 5 mg of Form A. After 24 hours, collect the solid by filtration and dry to give the title compound.

Example 21

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.10 g) in methanol (2.0 mL). Seal and stir at ambient temperature. After 30 minutes, add 5 mg of Form A. After 24 hours, collect the solid by filtration and dry to give the title compound.

Example 22

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (3.0 g) in ethanol (60.0 mL). Seal, heat to 40° C. and stir. After 24 hours, cool to ambient temperature. Collect the solid by filtration and dry to give the title compound.

Example 23

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione amorphous material (characterized by X-ray diffraction patterns without discernable peaks and microscopy analysis under cross-polarized light which showed little to no birefringence) (30 mg) in tetrahydrofuran (1.0 mL). Seal and stir at ambient temperature. After one week, collect the solid by filtration and dry to give the title compound.

Example 24

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione amorphous material (characterized by X-ray diffraction patterns without discernable peaks and microscopy analysis under cross-polarized light which showed little to no birefringence) (20 mg) in acetone (1.0 mL). Seal and stir at ambient temperature. After six days, collect the solid by filtration and dry to give the title compound.

Example 25

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione amorphous material (characterized by X-ray diffraction patterns without discernable peaks and microscopy analysis under cross-polarized light which showed little to no birefringence) (0.3 g) in acetone (15.0 mL). Seal and stir at ambient temperature. After six days, collect the solid by filtration and dry to give the title compound.

Example 26

(R)-3-(2,3-Dihydroxypropyl)-6-fluoro-5-(2-fluoro-4-iodophenylamino)-8-methylpyrido[2,3-d]-pyrimidine-4,7(3H,8H)-dione Form A Suspend (R)-3-(2,3-Dihydroxypropyl)-6-fluoro-5-(2-fluoro-4-iodophenylamino)-8-methylpyrido[2,3-d]pyrimidine-4,7(3H,8H)-dione (characterized by X-ray diffraction peaks at 22.61 and 18.42 degrees 2-theta and one endothermic event at 231° C.) (0.50 g) in ethanol (10 mL). Seal, heat to 50° C., and stir. After 30 minutes, add 25 mg of Form A. After 24 hours, cool to ambient temperature. Collect the solid by filtration and dry to give the title compound.

Example 27

(R)-3-(2,3-Dihydroxypropyl)-6-fluoro-5-(2-fluoro-4-iodophenylamino)-8-methylpyrido[2,3-d]pyrimidine-4,7(3H,8H)-dione Form A Dissolve (R)-3-(2,3-Dihydroxypropyl)-6-fluoro-5-(2-fluoro-4-iodophenylamino)-8-methylpyrido[2,3-d]pyrimidine-4,7(3H,8H)-dione (19.9 g) in acetic acid (0.8 mL) at 75° C., filter, and transfer into a preheated vial. Add toluene (1.5 mL in aliquots) and cool to ambient temperature at a rate of 20° C./h. After 24 hours, collect the solid by filtration, and dry in vacuo at ambient temperature to give the title compound.

What is claimed is:

1. A compound of the formula

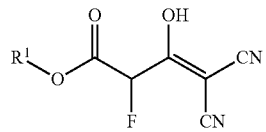

wherein $R^1$ is a suitable carboxy protecting group.

2. The compound of claim 1 wherein $R_1$ is methyl.

* * * * *